(12) United States Patent
Huber et al.

(10) Patent No.: US 8,306,666 B2
(45) Date of Patent: Nov. 6, 2012

(54) INTERACTIVE PATIENT SYSTEM

(75) Inventors: David Huber, Wollongong (AU); Craig Andrews, Mosman (AU)

(73) Assignee: David Huber, Wollongong (AU)

( * ) Notice: Subject to any disclaimer, the term of this patent is extended or adjusted under 35 U.S.C. 154(b) by 267 days.

(21) Appl. No.: 12/599,887

(22) PCT Filed: May 14, 2008

(86) PCT No.: PCT/AU2008/000704
§ 371 (c)(1),
(2), (4) Date: Nov. 12, 2009

(87) PCT Pub. No.: WO2008/138074
PCT Pub. Date: Nov. 20, 2008

(65) Prior Publication Data
US 2011/0125330 A1    May 26, 2011

(30) Foreign Application Priority Data

May 15, 2007   (AU) ................................ 2007902577

(51) Int. Cl.
*G05B 13/00*    (2006.01)
(52) U.S. Cl. ..... 700/275; 700/280; 600/301; 340/573.5; 5/713
(58) Field of Classification Search .................. 700/275; 600/300, 301; 128/897; 340/573.5
See application file for complete search history.

(56) References Cited

U.S. PATENT DOCUMENTS

| | | | |
|---|---|---|---|
| 6,287,253 B1 | 9/2001 | Ortega et al. | |
| 6,910,238 B2 * | 6/2005 | Biggie et al. | 5/713 |
| 7,378,975 B1 * | 5/2008 | Smith et al. | 340/573.1 |
| 7,849,545 B2 * | 12/2010 | Flocard et al. | 5/713 |
| 8,111,165 B2 * | 2/2012 | Ortega et al. | 340/573.5 |
| 2004/0261182 A1 | 12/2004 | Biggieet et al. | |
| 2009/0209830 A1 * | 8/2009 | Nagle et al. | 600/301 |
| 2009/0275808 A1 * | 11/2009 | DiMaio et al. | 600/301 |

FOREIGN PATENT DOCUMENTS

| JP | 2007144007 A | * | 6/2007 |
|---|---|---|---|
| JP | 20071440079 | | 6/2007 |

OTHER PUBLICATIONS

AU Intellectual Property Office International Preliminary Report on Patentability dated Sep. 7, 2009 for Application No. PCT/AU2008/000704.

* cited by examiner

*Primary Examiner* — Dave Robertson
(74) *Attorney, Agent, or Firm* — Colin P. Cahoon; Celina M. Orr; Carstens & Cahoon, LLP

(57) ABSTRACT

The present invention provides an interactive patient system comprising: apparatus; sensing means associated with the apparatus, the sensing means adapted to send, receive or identify a location signal; presence identification means associated with a region of a patient, the presence identification means adapted to send, receive or identify a location signal; and altering means adapted to alter a property of the apparatus in proximity to the presence identification means upon identification of an activity signal, thereby effecting an activity in the vicinity of the region of the patient, wherein the activity signal is associated with transmission or identification of at least one location signal as between the sensing means and the presence identification means. Also provided is a method for providing a directed response to a region of a patient.

17 Claims, 11 Drawing Sheets

Inlet port   Exhaust Port   Bi-Metal Strip Idle

Inlet port   Exhaust Port   Bi-Metal Strip Active

INTERACTIVE PATIENT SYSTEM

FIELD OF THE INVENTION

The present invention generally relates to interactive patient systems. More specifically, the present invention relates to interactive patient systems adapted to alter a property of an apparatus in proximity to a region of a patient.

BACKGROUND TO THE INVENTION

Pressure ulcers are a costly problem affecting patients undergoing acute or chronic treatment. Damage to localised areas of skin and underlying tissue can result from decreased perfusion to the affected areas due to pressure, sheer force, and/or friction. For example, the average sacral pressure on standard hospital mattresses is around 100-150 mmHg, while normal capillary filling pressure is around 32 mmHg such that even patients without vascular disease are at risk of developing ulcers.

The effect of pressure on regional perfusion has been widely investigated and it appears that localised pressure must be removed to decrease the incidence of ulcers.

There are several important risk factors which lead to decreased skin perfusion, or which directly damage the skin, the most significant of which is immobility leading to increased pressure on bony prominences. Other risk factors include incontinence (leading to skin maceration and increased likelihood of damage due to friction), age, malnutrition, and female gender.

Risk assessment is an important preliminary step to determining and instigating appropriate prevention and/or treatment regimes. However, ulcer risk assessment is difficult because there is little evidence that the available tools for assessment of risk are reliable or valid. The Braden scale, the Norton Risk Assessment score and the Waterloo Risk Assessment tool are examples of risk assessment tools utilised clinically in various countries.

The reliability of these assessment tools depends on the individual who takes the readings, and appropriate risk cut-off scores, among other things (see Australian Wound Management Association (2001) "Clinical Practice Guidelines for the Prediction and Prevention of Pressure Ulcers (abridged version)"). Despite these potential stumbling blocks, risk assessment is important because the appropriate prevention techniques depend on risk level, and both over and under-treatment are costly.

Several prevention techniques have been suggested, including the use of Australian Medical Sheepskin, 'low-tech' surfaces such as foam mattresses, 'high-tech' surfaces such as alternating pressure mattresses, and others, for instance, repetitively changing a patient's position and/or turning mattresses over and/or regularly repositioning patients.

Pressure care devices that are currently on the market can, for convenience, generally be divided into 'low-tech' and 'high-tech' devices. Examples from each group are listed below:

Low-Tech Devices
I. Standard foam mattresses;
II. Alternative foam mattresses/overlays (eg, high-specification foam, viscoelastic material, convoluted foam, cubed foam). These are conformable and aim to redistribute pressure over a large contact area;
III. Gel-filled mattresses/overlays;
IV. Fluid-filled mattresses/overlays;
V. Fibre-filled mattresses/overlays; and
VI. Air-filled mattresses/overlays.

High-Tech Devices
I. Alternating pressure (AP) devices. Typically, the patient lies on a grid of air-filled sacs which sequentially inflate and deflate, relieving pressure at different anatomical sites for short periods;
II. Air fluidised devices. Warmed air is circulated through fine ceramic beads covered by a permeable sheet. These devices allow support over a large contact area;
III. Low air loss (LAL) devices. Typically, patients are supported on a grid of air-filled sacs which are inflated at a constant pressure and between which air can be transferred; and
IV. Turning beds/frames (eg, kinetic or profiling beds). These beds typically either aid manual repositioning of the patient, or reposition the patient by motor-driven turning and tilting.

As can be appreciated, when incorporated into an institution-wide prevention program, including patient risk assessment and attention from trained staff, pressure ulcer prevention becomes costly. Furthermore, when prevention fails, ulcer treatment increases the cost and the length of stay in hospital. Complications of decubitus ulcers include cellulitis, osteomyelitis and sepsis.

Recent estimates from 365 US hospitals report ulcer incidence at 14.8% in hospital patients at a cost of between US$3.6 and US$8.5 billion. Indeed, the incremental cost of pressure ulcers related to hospitalisation for each patient has been estimated at US$12,186.

The low-tech and high-tech devices listed above and other prior art devices used in the treatment and/or prevention of pressure ulcers do not (and cannot) identify a given region of the body and cannot administer different affects and/or treatment regimes to different parts of the body differently or to the same or similar region of the body if the patient moves around the devices or objects with which the devices are associated.

The region or regions of interest typically vary from patient to patient and also depending on the type of treatment that is being administered, and the reasons why the patient is in hospital or at risk of developing pressure ulcers, among other things. For example, a patient who is otherwise well and is having a total hip replacement will require different management compared with a demented patient with peripheral arterial disease.

Indeed, current evidence of the use of the abovementioned devices, and in particular, the mattresses, suggests that none of them are especially efficacious at reducing the incidence of pressure ulcers (McInnes et al (2006) "Support surfaces for pressure ulcer prevention", Issue 3, The Cochrane Database of Systemic Reviews).

The present inventor has developed an interactive patient system and apparatus that is adaptable for use in a number of clinical and domestic situations.

SUMMARY OF THE INVENTION

According to a first aspect, the present invention provides an interactive patient system comprising:
apparatus;
sensing means associated with the apparatus, the sensing means adapted to send, receive or identify a location signal;
presence identification means associated with a region of a patient, the presence identification means adapted to send, receive or identify a location signal; and altering means adapted to alter a property of the apparatus in proximity to the presence identification means upon identification of an activity signal, thereby effecting an activity in the vicinity of the region of the patient, wherein the activity signal is associated with transmission or identification of at least one location signal as between the sensing means and the presence identification means.

Preferably, transmission or identification of at least one location signal as between the sensing means and the presence identification means is effected when the presence identification means and the sensing means are brought within a predetermined distance from one another.

Preferably, the apparatus is selected from a bed, a mattress, a pressure cushion, an underlay, an overlay, an orthosis, calliper, splint or crutch, or any other object or device that is brought into contact with, or comes in proximity to, a region of a patient, including any one or more of the low-tech or high-tech devices described above in the "Background to the Invention" section of this specification.

In a particularly preferred embodiment, the apparatus is a mattress. The mattress may be, for example, a foam mattress, formed of low density foam, high density foam, or a combination of low density and high density foams, and the foam mattress can be formed of multiple foam cells or compartments, a gel mattress, including with one or more cells or compartments containing a gel, an air mattress, including with one or more cells or compartments containing air, a spring mattress, or a combination of these or modular forms of one or more of these. The mattress may also be any one or more of the mattresses described above in the "Background to the Invention" section of this specification.

In some embodiments, the apparatus is an overlay or an underlay or a combination of an overlay and an underlay. The overlay and/or underlay may be, for example, a mattress protector, an incontinence sleeve or cover, an electric blanket, a support or cushioning means that is adapted to engage, for example, an orthosis, calliper, splint, crutch, mattress, seat or other related person support apparatus, a device specifically adapted to perform the functions of, or partially or fully house, the altering means, or any other overlay and/or underlay which is associated with an object or device that is brought into contact with, or comes in proximity to, a region of a patient.

The presence identification means of preferred embodiments is/are adapted to be placed in proximity to, or to be attached to, a region of a patient. In a preferred embodiment, the presence identification means is/are adapted to be sewn into, attached to, or housed by, a garment. In yet still further preferred embodiments, the presence identification means is housed by, or attached or connected to, an adhesive, such as a dressing or other adhesive adapted to adhere to the skin of a patient. The region of the patient in proximity with which the presence identification means is placed may be, for example, any region, but preferably is a region at risk of forming a pressure ulcer, such as, on or adjacent a bony prominence.

The location signal is preferably a signal or message of any kind capable of identifying the location of the presence identification means, even if the location is identified by reference to the presence identification means being within a predetermined distance from the sensing means.

The presence identification means of preferred embodiments can be any means capable of sending or receiving the location signal. In particularly preferred embodiments, the location signal is sent to, or received by, the sensing means associated with the apparatus. The sensing means are also adapted to send or receive location signals.

Preferably, in this way, the presence identification means and the sensing means "communicate" with one another via the location signal such that the sensing means "senses" or "detects" the presence of the presence identification means at a particular location, or within a predetermined distance or radius from the sensing means.

In particularly preferred embodiments, the presence identification means is a transponder and the sensing means is a reader.

Broadly speaking, transponders can be divided into three categories: active, semi-active, and passive. However, other categories or subcategories are identifiable for transponders, including passive coded, among others.

A transponder is said to be "active" if it has its own power source. The active transponder "pings" its identification periodically and the sensing means or reader, "listens" for any transponders within a predetermined distance or field. If the active transponder "pings" frequently, it is detected quickly by the reader. The more frequent the "ping", the greater the use of power, and in battery powered active transponders, the faster the battery expires. If the transponder "pings" less frequently, there will be some delay before it is detected by the reader, however, the battery lasts longer.

Active transponders typically have relatively longer range than other types of transponders. As would be appreciated by the skilled addressee, if the range is too great, the reader may detect the presence of the transponder even when not approaching the reader. Active transponders are also typically larger than other types of transponders, they are typically more costly and have a relatively short battery life.

The transponder is said to be "semi-active" if it has its own power source that is activated by an integral passive transponder circuit means receiving its energy from a reader's "interrogation". Semi-active transponders are, for example, typically used as part of an electronic toll booth collection system.

A transponder is said to be "passive" if it does not contain its own power source. Passive transponders preferably draw power from a nearby field, such as an electromagnetic field, provided by a reader, or sensing means. The reader "interrogates" an adjacent field for transponders that may be in its proximity and induces enough energy into the transponders electronic circuitry that allows the transponder to transmit back to the reader a data string that may include its identification number, or another form of location signal, as well as any additional data it may have stored in its memory.

An example of a simple passive transponder is a magnet. An example of a sensing means suitable for use with such a presence identification means is a Hall Effect sensor. The magnet can provide at least two states respectively associated with North and South poles, permitting administration of at least two therapeutic regimes.

Passive transponders are typically relatively smaller, have a smaller range, are cheaper and rarely need a battery change or replenishment of power source as compared to other types of transponders. Passive transponders are, for example, typically used for identification labels likely to be scanned at close proximity.

The system of the present invention contemplates using one or more of the abovementioned forms of presence identification means. However, other suitable presence identification means can also be used. Preferably, the system utilises passive transponders as presence identification means.

In some preferred embodiments, the presence identification means further includes data storage means adapted to store information relating to, for example, a preferred treatment modality or to patient specific information, including, for example, demographic data, health status and medical history.

The sensing means or reader preferably emits a low-frequency magnetic field via an antenna or coil. When the transponder comes within a predetermined distance from the reader, it is activated, causing transmission of a location signal, or its code, back to the reader. Preferably transmission and reception occurs simultaneously allowing for a very short read time.

As would be appreciated by persons skilled in the art, there are a vast number of ways in which the presence identification means and sensing means could "communicate" with one another such that the sensing means is able to "detect" or "sense" the presence of the presence identification means within a predetermined distance or proximity. The present invention contemplates all such alternative arrangements.

In this, specification, words including "communicates", "interrogates", "senses", "detects", "reads", "listens", "interferes" and "disturbs" are used when describing the manner in which the presence identification means and the sensing means interact with each other and/or when describing the activities in which the presence identification means and/or sensing means engage in order to interact with one another. Depending on the context, these words may be used interchangeably or mutually exclusively. However, persons skilled in the art would appreciate that in no event does the use of one such word limit the scope or meaning of another of such words or of another word not necessarily used herein, that may, because of the context, the kind of presence identification means used or the kind of sensing means used, better describe the manner in which the presence identification means and the sensing means interact and/or better describe the activities in which the presence identification means and/or the sensing means engage in order to interact with one another.

In some preferred embodiments, for example, the location signal is created and/or generated and therefore (or then) "communicated" between the presence identification means and the sensing means when the presence identification means and the sensing means are brought within a predetermined distance from one another. In one such embodiment, the presence identification means will "disturb" a field, for example, an electro-magnetic field, on or around the sensing means and/or the sensing means will "disturb" a field, for example, an electro-magnetic field, on or around the presence identification means, when the presence identification means is brought within the predetermined distance from the sensing means or vice versa as the case may be. This "disturbance" enables detection of the presence identification means by the sensing means or vice versa as the case may be.

As would therefore be appreciated by persons skilled in the art, when the word "send" is used in relation to the manner in which a location signal is communicated from the presence identification means or the sensing means, the "sending" of the location signal includes, but is not limited to, transmitting, emitting, giving off, radiating, transferring, conveying, delivering and interrupting or disturbing a field when present within that field, or any other manner in which a location signal of any kind could be sent from the presence identification means or the sensing means.

Similarly, when the word "receive" is used in relation to the manner in which a location signal is communicated to a sensing means or a presence identification means, the "receiving" of the location signal includes, but is not limited to, accepting, acknowledging, acquiring, admitting, appropriating, assuming, identifying, deriving, obtaining, taking in, and having a field disturbed by the presence of something in that field, or any other manner in which a location signal of any kind could be communicated to a sensing means or a presence identification means.

In yet still further preferred embodiments, the presence identification means and sensing means are each adapted to "communicate" (via, for example, receiving or sending) a location signal through a control means which itself is adapted to regulate and control the activities of the interactive patient system of the present invention. In some such embodiments, the control means is adapted to facilitate, or give direction to, the altering means.

The control means of some preferred embodiments is adapted to identify an instruction from the presence identification means and/or the sensing means and to send an activity signal to the altering means to alter the property of the apparatus.

In particularly preferred embodiments, the property of the apparatus altered in response to the activation signal is selected from pressure, temperature, movement, vibration, a combination of these, or any other property that would be desirable to alter in the context of treating and/or preventing a condition in a patient, including, for example, pressure ulcers.

In one preferred embodiment, the activity effected in the vicinity of the region of the patient is an increase or reduction in pressure. In yet another preferred embodiment, the activity is vibration and in another preferred embodiment, the activity is a change in temperature. In yet still further preferred embodiments, multiple different activities are effected in the same or similar vicinity of the region of the patient at any one time.

The relevant activity can be achieved by a range of mechanisms effected by the altering means. In some preferred embodiments wherein the activity is a change in pressure, the pressure may be increased or decreased by the altering means causing, for example, advance or withdrawal of a part of the apparatus where the change in pressure is required or adjacent the relevant presence identification means (eg the presence identification means "sensed" by the sensing means). The altering means can take any suitable form to achieve the relevant alteration in property of the apparatus that would give effected to the relevant activity. For example, if the apparatus has one or more air cells or enables the flow of air, the altering means can take the form of a pump adapted to provide negative pressure to cause withdrawal and positive pressure to cause advance. Alternatively, if, for example, the apparatus is a spring mattress, the altering means can take the form of an actuation member operably engaged with at least one spring and adapted to retract or extend the spring as required.

In some preferred embodiments wherein the activity is a change in temperature, the altering means can take the form of a heater or cooler. In other preferred embodiments wherein the activity is vibration, the altering means can take the form of a vibration means. In preferred embodiments wherein the activity is movement, the altering means can take any suitable form to effect the relevant movement. The altering means of some preferred embodiments takes multiple forms so that it is capable of giving effect to multiple different activities simultaneously.

In some preferred embodiments, the property of the apparatus is altered in proximity to the presence identification means. Preferably, the sensing means is associated with the apparatus, thereby "detecting" or "sensing" the location of the relevant presence identification means relative to a particular part of the apparatus. Preferably, the system is adapted so that it is capable of effecting different activities in the vicinity of different regions of the patient when such regions are respectively in a particular proximity to a relevant part of the apparatus.

It may be desirable, for example, that a particular part of an apparatus on which a patient is adjacent or resting be physically altered so as to avoid contact with a proximate region of the patient. In one preferred embodiment, this is achieved by causing that part of the apparatus to retract or, for example, deflate, when a sensing means adjacent that part of the apparatus "senses" that a presence identification means associated with that region of the patient is in proximity to (or within a predetermined distance from) the sensing means. In another preferred embodiment, the same or similar effect is achieved when one or more parts of the apparatus adjacent the part of the apparatus which must be prevented or inhibited from contacting the region of the patient are caused to advance toward the patient or, for example, inflate so that the region of the patient which is to be prevented or inhibited from making contact with the apparatus is pushed or lifted away from the apparatus.

In preferred embodiments, the system operates so that if the region of the patient moves relative to the surface of the apparatus on which or in proximity to which the region of the patient is located, the property or properties of the apparatus adjacent the region of the patient that are to be altered by the altering means are so altered as the movement occurs. In some such preferred embodiments, different parts of the apparatus will have their property or properties altered as the region of the patient moves relative to the apparatus. In this way, one or more activities are effected by the system in line with the movement of the region of the patient.

The activity signal of preferred embodiments is any signal capable of "informing", or transmitting data, information or energy to the altering means to alter the property of the apparatus. In one preferred embodiment, the activity signal is an electrical impulse. In another preferred embodiment, the activity signal is a change in voltage, current, frequency or resistance. In further embodiments, the activity signal is a wireless signal, such as a radio frequency signal.

In some preferred embodiments, transmission of the activity signal is delayed for a predetermined period so that a relevant altered activity is partly or wholly prevented or inhibited from interfering with the patient's ability to obtain a comfortable position relative to the apparatus.

In further preferred embodiments, the system is adapted to additionally provide one or more predetermined and/or preprogrammed altered activities to a property of the apparatus, wherein the predetermined and/or preprogrammed altered activity or activities is not necessarily related to communication or interaction between a particular presence identification means and sensing means. Such predetermined and/or preprogrammed altered activity can be inputted into the system by an operator. In one preferred embodiment, the predetermined and/or preprogrammed activity is adapted to provide a turning-type movement to a patient so as to alternate raising each side of, or a portion of, the patient. Such activity may be desirable, for example, in a patient who is immobile and supine on a bed or mattress surface for prolonged periods of time.

According to a second aspect, the present invention provides a method for providing a directed response to a region of a patient, the method comprising:

providing an apparatus according to the first aspect of the present invention;

attaching the presence identification means adjacent the region of the patient;

placing the patient on, or in operative proximity to, the apparatus; and enabling the altering means to alter a property of the apparatus in proximity to the region of the patient in response to an activity signal, thereby providing a directed response to the region of the patient.

According to a third aspect, the present invention provides an interactive apparatus for patient care comprising:

apparatus;

altering means adapted to alter a property of the apparatus;

sensing means associated with the apparatus, the sensing means adapted to send or receive a location signal;

presence identification means associated with a region of a patient, the presence identification means adapted to send or receive a location signal; and controlling means adapted to identify an instruction from the sensing means or presence identification means and to cause the altering means to alter a property of the apparatus in proximity to a region of a patient.

According to a fourth aspect, the present invention provides a method for providing a directed response to a region of a patient, the method comprising:

providing an apparatus according to the third aspect of the present invention;

attaching the presence identification means adjacent the region of the patient;

placing the patient on, or in operative proximity to, the apparatus; and enabling the controlling means to cause the altering means to alter a property of the apparatus in proximity to the region of the patient in response to the location signal, thereby providing a directed response to the region of the patient.

According to a fifth aspect, the present invention provides region location identification means adapted to be associated with a region of a patient, the region location identification means comprising:

presence identification means adapted to send or receive a location signal to or from sensing means; and position maintenance means adapted to maintain the presence identification means in proximity to the region of the patient.

In a preferred embodiment, the presence identification means is a transponder. In some preferred embodiments, the presence identification means is substantially housed by the position maintenance means.

In another preferred embodiment, the position maintenance means includes an adhesive, or an item of clothing or a part of an item of clothing.

Preferably, the region location identification means is in the form of a patch which can be adhered to, or maintained in proximity to, the region of the patient.

According to a sixth aspect, the present invention provides a cell for use in an interactive patient system, the cell adapted to alter a property by changing from a first state to a second state in response to an activation signal. Preferably, the cell is adapted to be incorporated into the apparatus and/or altering means of the first aspect or second aspect of the invention.

In one preferred embodiment, the property altered relates to a pressure which the cell applies to or receives from a region of a patient in the vicinity of the cell. In such an embodiment, the first state is an increase pressure state and the second state is a decrease pressure state. Preferably, the cell functions by movement of fluid transforming between an emptying condition, the decrease pressure state, and a fill condition, the increase pressure state.

The fluid can be a liquid or gas. In a preferred embodiment the fluid is a gas. In such embodiments, when the cell is in the emptying condition, substantially all of the gas contained in the cell has been expelled from the cell. When the cell is in the fill condition, a volume of the cell is substantially full of gas. In a preferred embodiment, a solenoid under the control of control means acts to regulate the flow of gas in or out of the cell.

The cell may be a part of a matrix of cells joined together in fluid communication. In some embodiments, the cell or matrix of cells is additionally fluidly joined to pump.

According to a seventh aspect the present invention provides an interactive patient system comprising:

apparatus;

sensing means associated with the apparatus, the sensing means adapted to send or receive a location signal;

presence identification means associated with a region of a patient, the presence identification means adapted to send or receive a location signal; and altering means adapted to alter a property of the apparatus in proximity to the presence identification means upon identification of an activity signal, thereby effecting an activity in the vicinity of the region of the patient.

Preferably, the activity signal is associated with transmission or identification of at least one location signal as between the sensing means and the presence identification means.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field of the invention In order that the present invention may be more clearly understood, preferred embodiments will be described with reference to the following drawings and examples.

BRIEF DESCRIPTION OF THE DRAWINGS

The invention will now be further explained and illustrated by reference to the accompanying drawings in which.

DETAILED DESCRIPTION OF PREFERRED EMBODIMENTS

In preferred embodiments, the system provides comfort and relief to a patient in bed by applying any combination of, but not limited to, heat or cooling, vibration, pressure relief, elevation and/or another form of treatment, to an affected area.

The affected area is identified by a transponder attached to the patient. Search coils embedded in the mattress or mattress overlay or underlay are used to locate the affected area of the patient to treat it accordingly.

A control means or controlling processor administers a selected treatment for the affected area periodically, as programmed by an operator, such as a hospital staff member.

Figure 1:
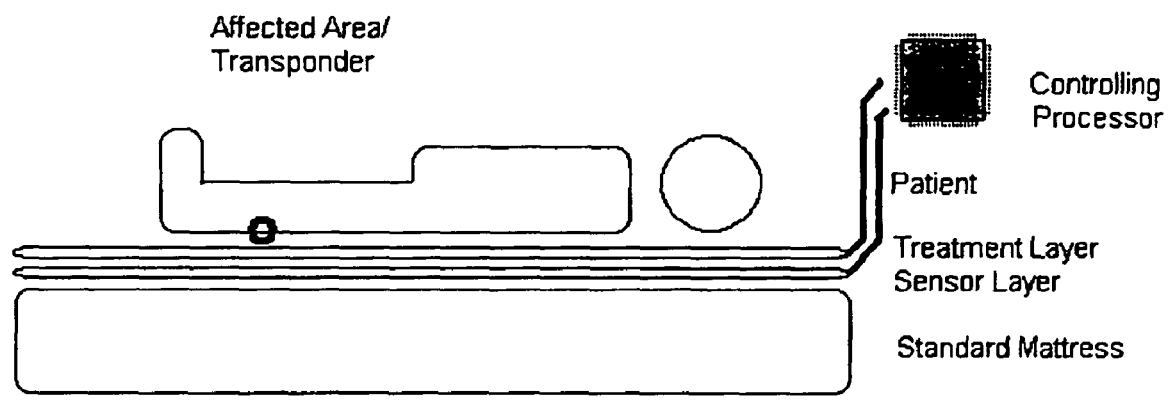
FIG. 1 is a schematic representation of the system of a preferred embodiment being a mattress.

As is illustrated in FIG. 1, the patient wears a presence identification means on or around the affected area requiring treatment. This provides a location reference for the affected area relative to the mattress. A sensing means or sensor layer is used to detect the location of this presence identification means. The location is then reported to a control means or controlling processor via transfer of a location signal. The processor then controls altering means or a treatment layer, providing the requested treatment.

Figure 2:
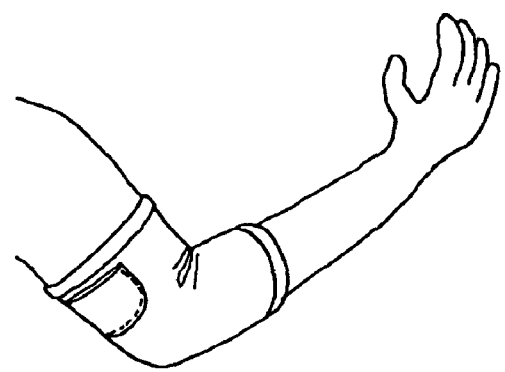
FIG. 2 is an illustrative example of a "sock" or "sleeve" style support adapted to house a transponder according to a preferred embodiment.

FIG. 2 illustrates a "sock" or "sleeve" type support adapted to house a presence identification means, such as a transponder, on or adjacent the affected area of the patient requiring treatment. The "pocket" or "patch" depicted on the back of the support may be adapted to hold, for example, the presence identification means, a power source, any other device or means which it may be desirable to maintain in proximity to the patient or the support, or a combination thereof. The presence identification means may also be embedded in such a support or in a garment.

The treatment layer will provide the desired activity, for example, heat, pressure relief, elevation and/or vibration, continually, at controlled intervals, on demand, or as programmed.

In a preferred embodiment, the system is adapted to be placed over the top of a mattress, without requiring a major change to the hospital environment.

In preferred embodiments, the presence identification means is a transponder. As mentioned above, passive transponders do not require a power source internal to the transponder. This will allow a thinner transponder, making the use of the transponder less intrusive. Active transponders have internal power, making them more expensive and bulky, but allow more flexibility in their features.

The passive transponder is preferably used for obtaining the position of a patient's particular appendage on the mattress. If more than one body part requires treatment a coded passive transponder is used to assign an ID to each additional transponder. The ID can then be associated with the body part to which the transponder is attached.

The active transponder is preferably used where monitoring some parameter of the patient is required. Single point measurements like temperature or pressure on the sensor, or humidity can be measured and transmitted to the control means or controlling processor.

Preferably, the transponder is attached to the patient to provide the system with location information. Several methods of attachment are possible for the different body parts and transponder types.

In one preferred embodiment, the transponder is placed on, or housed within, an adhesive layer that attaches to the patient's skin. In another embodiment, the transponder is attached to, or housed by, the patient's clothing, for example, by sewing the transponder into the clothing. In another embodiment for use with limbs, a sock or band can provide the means of connecting the transponder to the patient's limb. This could take the form of a knee support or thermal bandage. The transponder may be sewn into a sock support, or bandage, or placed in, for example, a velcro pocket. The velcro pocket approach is particularly useful where active transponders are used, which require a power source or batteries to be replenished or charged.

In broad terms, one preferred mechanism of operation of a passive transponder and active transponder is set out below:

Passive Transponder:
I. Sensor layer generates an RF (Radio Frequency) pulse from the search coil.
II. RF energy is absorbed by the transponder.
III. The search coil current (discussed in more detail below) will change for the cells under the transponder.
IV. The absorbed energy can be used to generate a coded pulse for identifying the transponder if required.

Active Transponder:
I. The sensor layer generates an RF pulse.
II. RF energy is received at the transponder.
III. The active transponder sends a coded pulse with required information to the sensor layer.

There are a number of different frequency standards available for transponder and reader communication, such as low frequency, for example, 125 KHz, high frequency, for example, 13.56 MHZ, and ultra-high frequency, for example, 900 Mhz. In some preferred embodiments, the present invention uses the 13.56 MHz standard. In preferred embodiments, this standard can provide an appropriate read range of around 8-14 cm depending on the transponder used.

The sensing means or sensor layer of preferred embodiments contains "search" coils used to generate an RF pulse to operate the transponder. The sensor layer will operate with either passive or active transponders.

In some such preferred embodiments, the sensing means or reader generates an alternating electromagnetic field at 13.56 MHz which provides the power supply for a passive transponder through electromagnet coupling. In some preferred embodiments, the electromagnetic field is also used as a carrier frequency for data transfer.

Preferably, the transponder consists of a microchip and a tuned (13.56 MHz) LC-oscillator that provides power to the microchip and is used as an antenna for communication. Communication between reader and transponder is achieved by modulation of the 13.56 MHz carrier frequency. Binary information (1 & 0) can be transferred by modulation of the reader and transponder antenna. Different amounts of binary information can be stored depending on the transponder used.

The geometry, size, antenna transmitter power and tuning quality factor of the reader and transponder antennas greatly influence the read distance, ie the maximum distance a reader and transponder can be separated and still communicate. Maximum read distance is typically achieved when the transponder is placed in the middle of the reader-antenna (middle of electromagnetic radiation) and on the same plane.

In preferred embodiments, the reader scans for transponders constantly and when a transponder is detected or sensed, data content of the detected transponder's memory can be transferred to a connected personal computer. Predefined data can be programmed into the transponder before use and this data could be used to inform or instruct alteration of a property of the apparatus following transmission of an activity signal. Such alteration and the activity or activities to which it or they give rise are discussed in more detail below.

Preferably, the sensor layer contains a matrix of search coils for locating the transponder worn by the patient. The level of resolution for the sensing process is increased by having a larger number of coils of a smaller diameter. The resolution is typically half the diameter of a coil. By overlapping the search coils, the resolution can be increased without reducing the range of the detection method. In one preferred embodiment a large number of coils of about 100-200 mm are used to detect the position of the transponder to a resolution of about 50-100 mm. This resolution is typically sufficient for resolution of the treatment layer.

In some embodiments, electronics are distributed in modules through the sensor layer. This distributed approach assists with reducing the signal to noise ratio associated with conductors running past the RF fields from the search coils.

The search coils may be used for both the transmission of the RF energy for the transponder and the detection of the transponder's signal (if any). In some preferred embodiments, the coils are made from winding wire, or as part of a flexible printed circuit board. The inductance of the coil is proportional to the square of the number of turns, according to the following formula:

$$L = \frac{r^2 N^2}{(2r + 2.8d) \times 10^5}$$

Where:
L=inductance in H
r=mean radius of coil in meters
N=number of turns
d=depth of coil in meters (i.e., outer radius minus inner radius)

The resulting magnetic flux is proportional to the inductance of the coil. The effective range of the inductive coupling to the transponder is proportional to the radius of the loop and a function of the position of the transponder over the coil. A wider coil will allow greater range, but a loss of resolution. The position of the transponder can be more accurately found by overlapping the coils with a voting scheme in the controlling processor.

Figure 3:
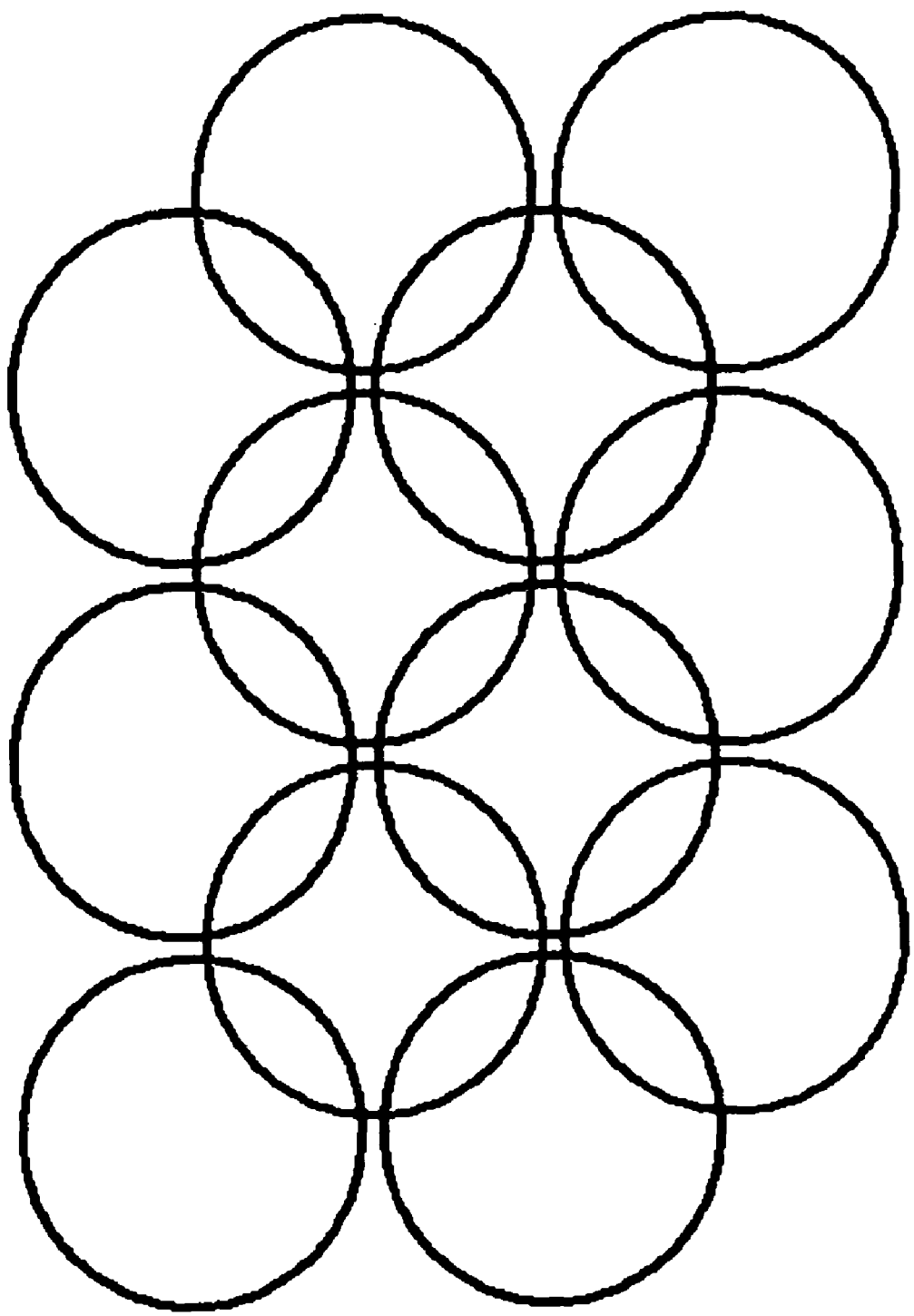
FIG. 3 illustrates the conceptual result of overlaying "search" or "detection" coils in the sensing means.

FIG. 3 shows the concept of overlaying detection coils.

Figure 4:
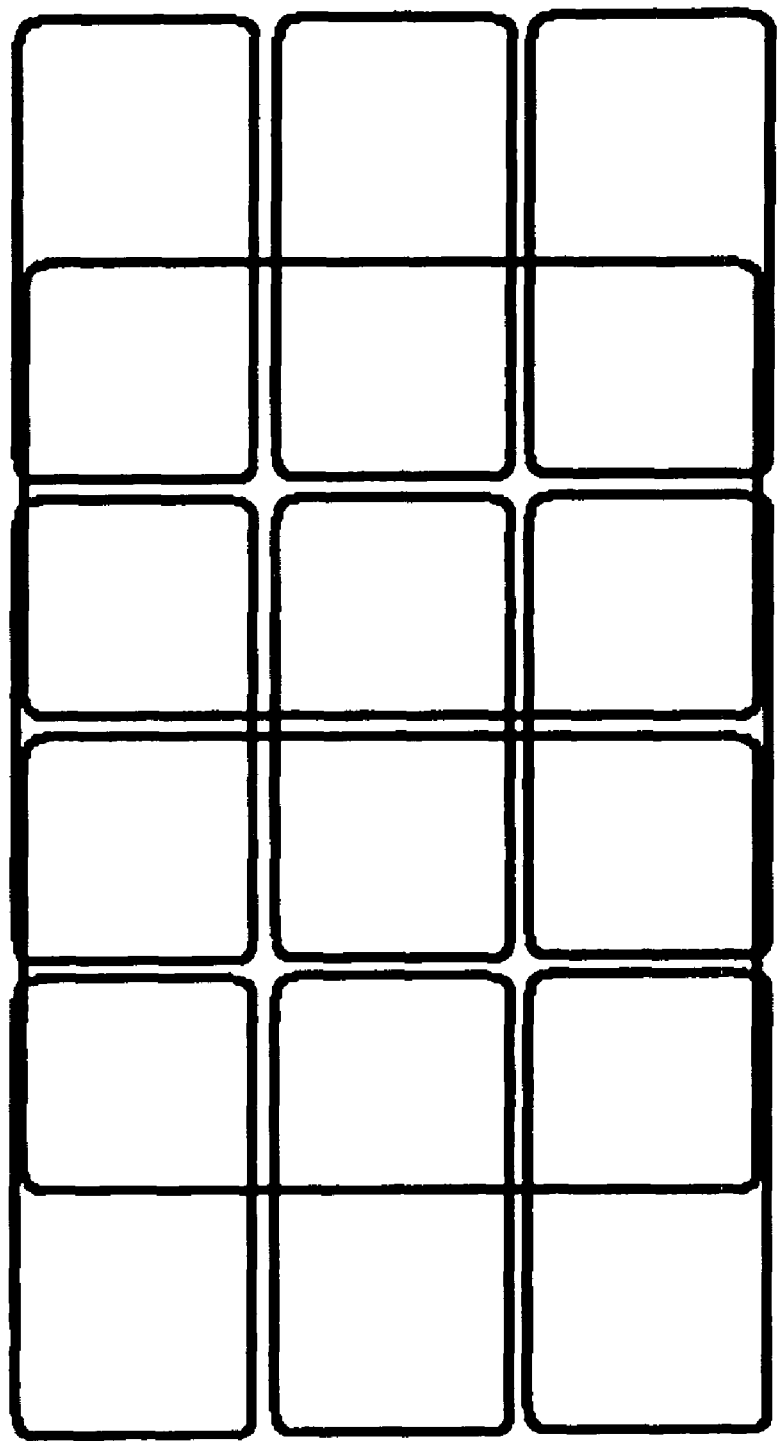
FIG. 4 illustrates the conceptual result of overlaying "search" or "detection" coils in the sensing means, wherein the coils are rectangular.

FIG. 4 shows rectangular coils in a different matrix. The rectangular matrix will allow more of an (x,y) decoding of the position of each respective transponder.

Detecting location signals from passive transponders requires a relatively high signal to noise ratio. The distributed electronics (discussed above) allow localised buffering of the drive signal and receive pulse/drive current used for detection. Some of the signal processing and control processing may also be performed by the distributed electronics.

In preferred embodiments, the control means or controlling processor provides a user interface and control algorithms. The processor may be a Personal Computer (PC), a Personal Digital Assistant (PDA) or an embedded microcontroller. The interface can be adapted for using RS232, RS485, USB, Bluetooth, WIFI or a variety of other protocols. A different communications module can be provided as needs change.

Figure 5:
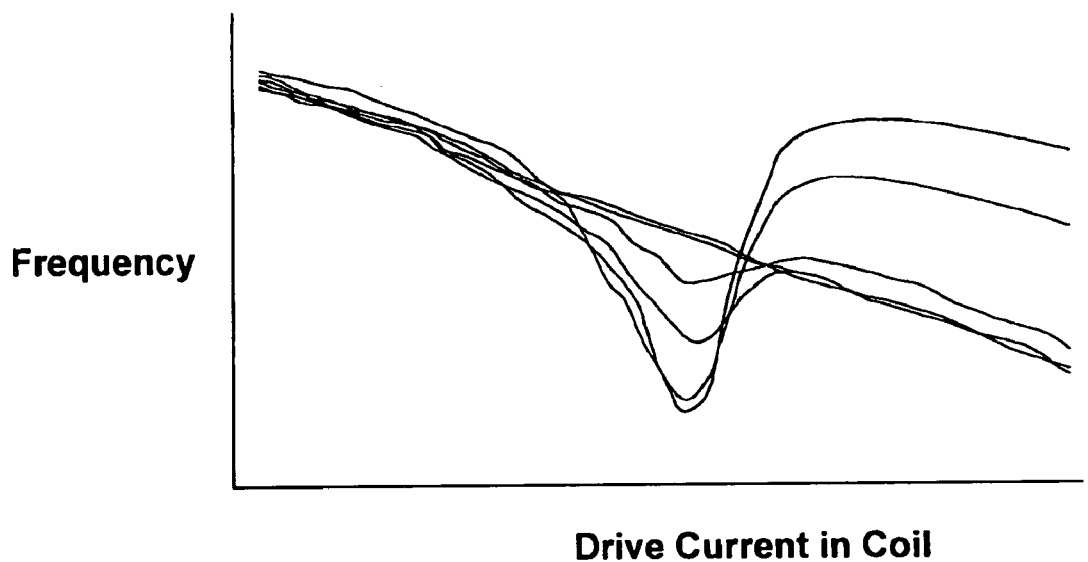
FIG. 5 is a graphical illustration of a "dip" in frequency associated with the change in drive current in a particular coil of the sensing means when a transponder comes within a predetermined distance from the coil.

Although some preferred embodiments have been described above, wherein the transponder used is a passive transponder, the operation of the search coils is different for the different types of transponder. Broadly speaking, the operation of the search coils will differ depending on the type of transponder used as follows:

Simple Passive: The location of the transponder can be found by "looking for" the dip in the drive current for a particular coil. This is a relative dip in frequency over a small scanning range of frequencies. FIG. 5 shows the drive current changing for the drive frequency when a tuned circuit transponder is nearby. This sweeping allows for very small amounts of signal to be detected from the range of measurements.

Coded Passive: In much the same way as tags used in supermarkets and libraries, the search coil drives the transponder and "listens" for a code to be echoed back to it.

Active Transponder: The active transponder sends a code back to the drive coil in the same way as the coded passive transponder. The difference being that there is a power source provided to allow measurements of the patient to be performed.

In preferred embodiments, altering means or a treatment layer provides the therapeutic benefit to the patient. Some of the preferred therapeutic options include, but are not limited to:

I. pressure relief and/or elevation (via, for example, pneumatic cell)
II. heat or cooling
III. vibration The treatment layer is preferably comfortable, whether or not treatment is being administered. In one preferred embodiment, for example, pressure relief and/or elevation is provided to any (or all) of a matrix of air cells. Associated with each air cell can be a heating element and vibration mechanism. The vibration, heat and air cell can be independently controlled by the control means or controlling processor, or can operate independently upon receipt of an activity signal.

One preferred air cell includes a bladder, an inlet valve, an outlet valve and a pump. The bladder is preferably an expandable (for example, provided by concertina or flexible material) chamber of air providing elevation to a location of interest on the patient following inflation. In one embodiment, the bladder is about 50 mm long×50 mm wide. The height dimension, incorporating inflation of the chamber or cell, is variable but typically falls within a range of about 5 mm (when empty) to about 100-150 mm (when full).

In embodiments where the bladder incorporates vibration and/or heating elements, they are preferably provided on an upper surface of the bladder.

The transfer of air through the various components of the air cell system is preferably provided by at least one conduit or hose or a series of conduits or hoses or a heat-staked manifold under the air cells.

The operation of the air cells in this embodiment includes a plurality of solenoid valves to control the air flow in and out of the cells. In other preferred embodiments, a bi-metal strip is used as a control mechanism for an exhaust valve, or to aid in controlling the movement of air through the air cell system.

The transfer of air can be 'managed' in the sense that an air flow control means regulates the flow or transfer of air through the components of the system. The air flow control means can operate under the control of the control means.

Figure 6:
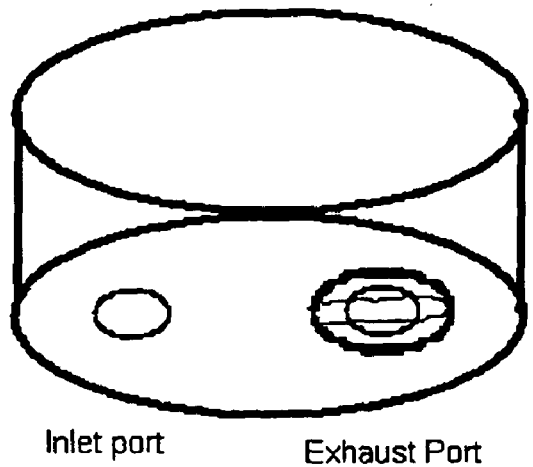
FIG. 6 is a two-part schematic illustration of the operation of a bi-metal strip exhaust port valve allowing air to enter or be released from an interactive device.
Figure 6:
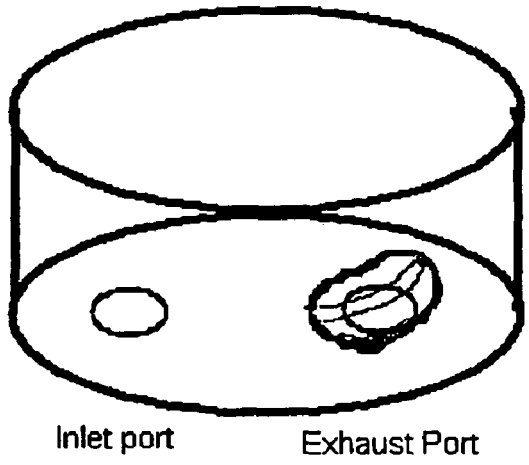

FIG. 6 illustrates the operation of the bi-metal strip exhaust port valve. When the strip is "idle", the pressure inside the air cell holds the flap over the mouth of the port. When the bi-metal strip is "active", the air from the cell is free to leave via the exhaust port.

In yet still further preferred embodiments, an "And-Valve" (based on the principle of the "AND gate" in electronics) is used as a means of controlling air flow. Note that the "AND gate" has a positive output if both of the inputs are positive. Similarly, the "And-valve" allows air flow if there is pressure on both sides.

Figure 7:
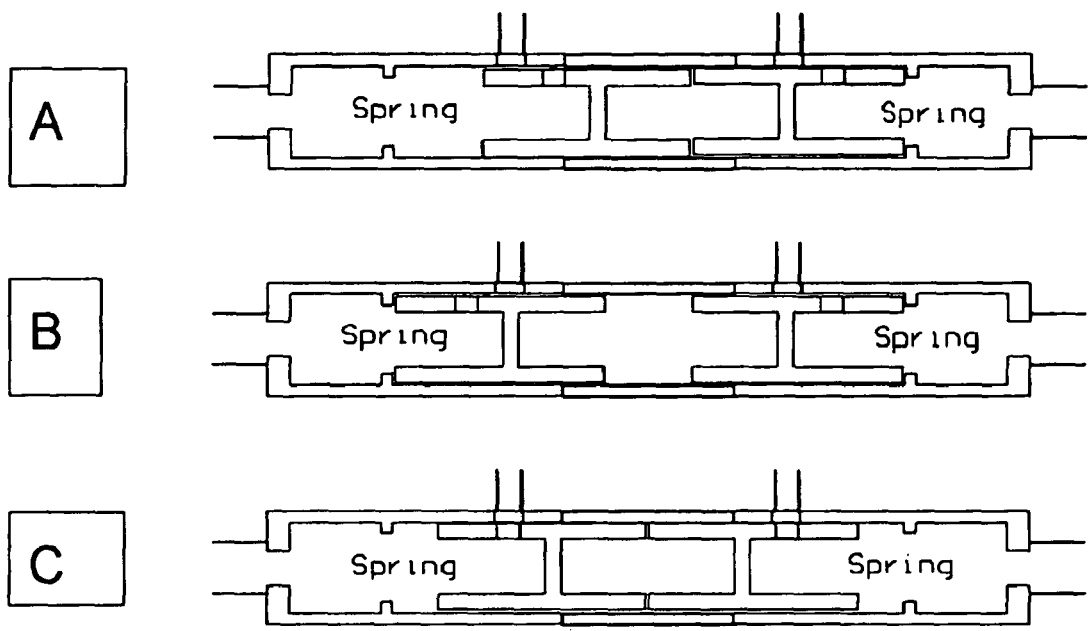
FIG. 7 is a three-part schematic illustration of the operation of an "AND valve".

There are essentially three states for the "And-Valve" as is illustrated in FIG. 7. Input ports are illustrated on the sides and the output ports are illustrated on the top of each represented state for the "And valve". The word spring denotes a tension spring.

The middle illustration in FIG. 7 (identified as "B") shows the valve in the rest state, in which there is no pressure on either half of the valve.

As pressure builds in the chamber, the piston moves away from the input port. The top illustration in FIG. 7 (identified as "A") shows the valve with pressure on one half of the valve. The piston is free to move past the point where the hole in the piston matches up with the exhaust port. The bottom illustration in FIG. 7 (identified as "C") shows the operation of the valve when equal pressure is applied to both halves. The springs compensate for the pressure difference.

Using the "And valve" in a multiplexed arrangement (with solenoid valves also) allows a considerable reduction in the number of solenoid valves required for operation.

Figure 8:
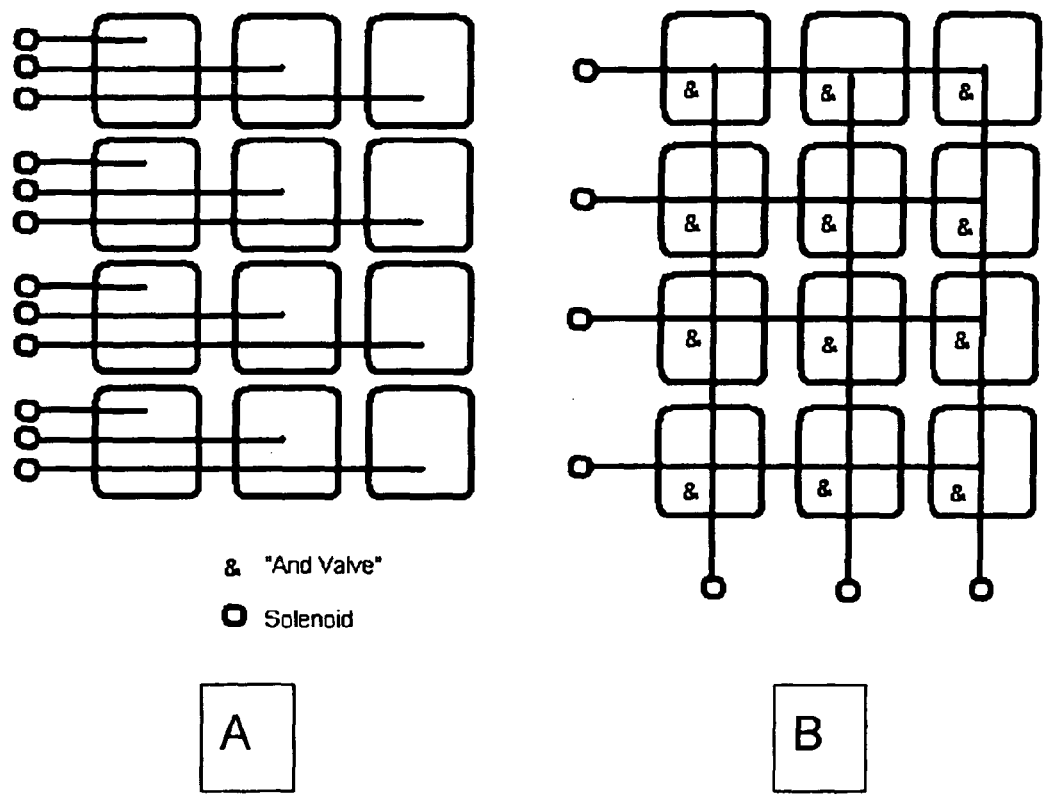
FIG. 8 provides a two-part comparative example of different valve arrangements for controlling air flow through a grid of 4×3 air cells.

FIG. 8 provides a comparative example of the arrangements required for a 4×3 air cell grid, respectively using solenoid valves only (identified as "A") and using "AND valves" and solenoid valves (identified as "B").

In embodiments incorporating the ability to provide heat, heating is preferably provided by a resistive element similar to an electric blanket, or, for example, by allowing a stream of hot air through the cell. By activating the inlet valve and the outlet valve a flow of heated air can be pumped through the cell. In such embodiments, the pressure of the cell is maintained by refraining from turning on the outlet valve all the time.

An alternative to the hot airflow model is to place a flexible resistive element on or near the top of the air cell. Wiring can be run to the heating element via the inside of the air cell.

In embodiments incorporating the ability to provide vibration, the vibration can be administered to the patient by, for example, embedding an eccentric cam motor at or near the top of the air cell.

To improve patient comfort, the electronic modules, valves and other components can be fitted into foam. The individual air cells can also have a layer of foam over the top to prevent the mechanism from causing discomfort.

As outlined above, in some preferred embodiments, a control means operates to control the activities of one or more elements of the system, for example, the sensing means, the altering means and a treatment schedule. By way of example:

Signals from the sensing means are processed to interpolate the position of the transponder.

The position is then used to identify the cell closest to the patient's affected area.

The control means or controlling processor then administers the treatment required at that particular cell by causing the altering means to alter the relevant property of the mattress (or other apparatus) in the relevant location. Different processors may perform these three tasks.

The user interface of preferred embodiments provides a mechanism for the user to control the settings and operation of the system. If using a PC, the user interface is implemented on a computer screen, for example, using a windows-based application to control the mattress. The inputs for the computer based user interface may be any combination of keyboard, mouse and touch screen. If the control means or controlling processor is an embedded micro-controller an interface is implemented, for example, on a liquid crystal display (LCD) and a series of buttons to enable the user to manipulate relevant data and program desirable treatment regimes.

Both control means and PC can implement a wireless protocol to a PDA for remote controlling of the user interface. This approach removes the need for an input or output device connected directly to the control means.

An indication of each transponder's location can be displayed on the user interface. The system or control means periodically checks the position of each transponder. The altering means or treatment layer can be reconfigured if the transponder position has moved.

It may be beneficial to treat the patient periodically rather than constantly. This may be handled by the control means in some preferred embodiments. The user interface provides the operator, such as a hospital staff member, with the means to control the treatment to be administered including, any timed treatments, dosing, and any other variables related to the treatment regime. The user interface also provides the user with feedback on how the system is performing. For example, the number of times the patient moves may provide a useful metric of discomfort.

In some preferred embodiments, the control means drives search coils to "find" each transponder's signal strengths in different cells. The geometry of the "search" coils, their physical position and the respective signal strength detected for each transponder allow the transponder position (and, possibly, its distance from the mattress) to be estimated.

The position of the transponder is converted to the position of the nearest air cell. This is the "cell address" for the possible treatments. The cell address may be different for different mattresses capable of different treatments.

Figure 9A:
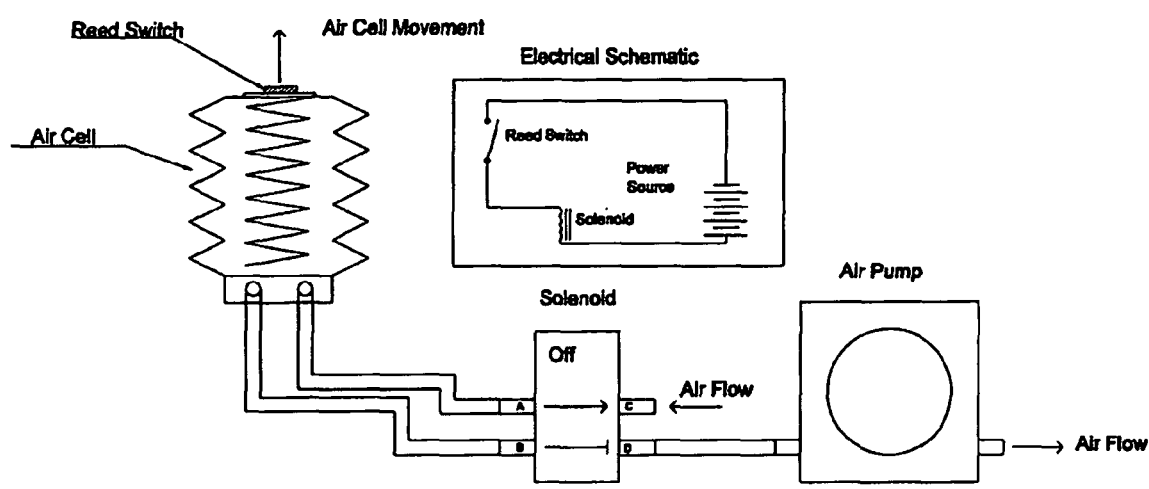
FIG. 9A is a schematic illustration of one embodiment of a cell adapted to be incorporated into the apparatus of preferred embodiments.
Figure 9B:
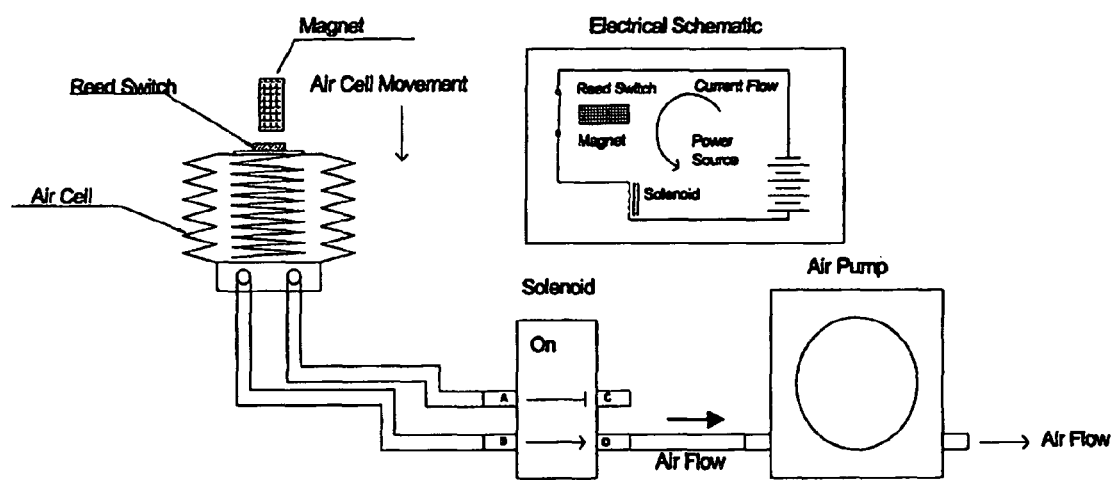
FIG. 9B is a further schematic illustration of the cell depicted in FIG. 9A wherein the cell is transforming from the fill condition into the emptying condition.

FIGS. 9A and 9B are schematic illustrations of a cell, in the form of an air cell, according to a preferred embodiment of the invention along with its corresponding electrical circuit. Only one air cell is shown in the schematic, however any number of air cells may be connected in accordance with the invention. In a preferred embodiment each air cell has its own solenoid and reed switch.

When no transponder is in proximity to the reed switch, the cell is in a rest state. As illustrated in FIG. 9A, in such a circumstance, the air cell is inflated and in the air fill condition due to the internal spring drawing air through ports C and A of the solenoid and into the air cell. Port B is blocked from the vacuum on the port D side of the solenoid created by the air pump. The electrical path is opened and no current flows through the solenoid.

The schematic illustration in FIG. 9B shows the cell in the activated state with a presence identification means in the form of a simple transponder (operating as a magnet) in close proximity to the reed switch. The magnetic flux causes the reed switch to close allowing current to flow through the circuit. Activation of the solenoid allows air to flow from port B to port D. Port A of the solenoid is now blocked from port C and air sucked out of the air cell by the vacuum created by the air pump. The air cell therefore transforms from the air fill condition to the air emptying condition.

Figure 10A:
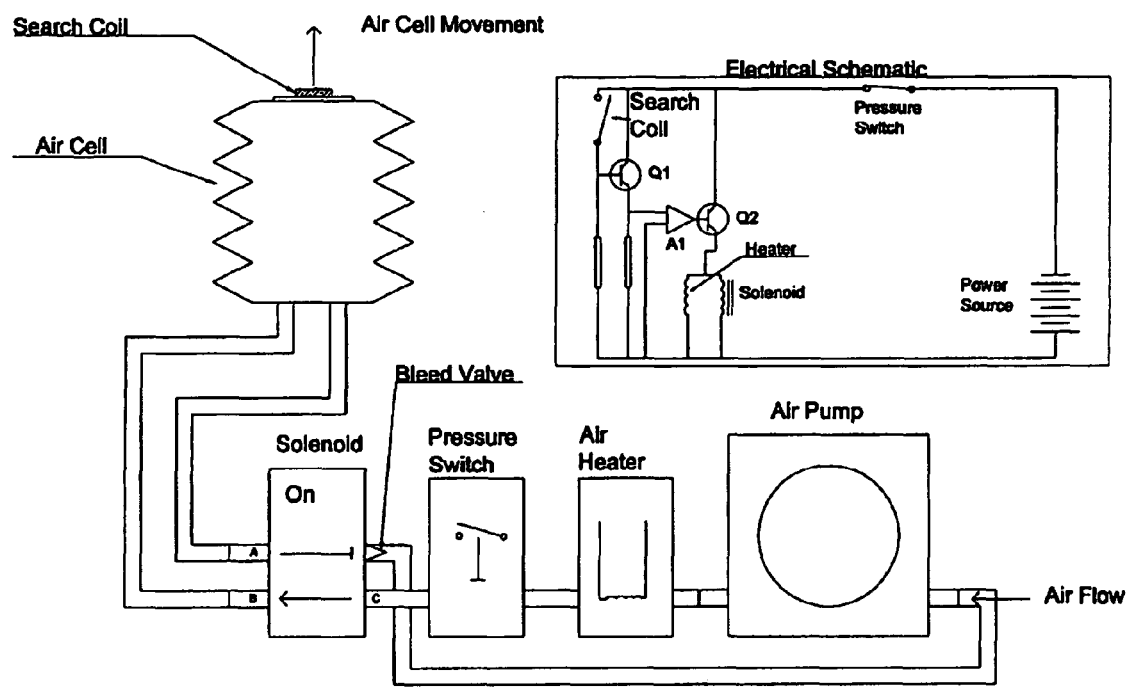
FIG. 10A is a schematic illustration of a mechanism of cell operation according to another preferred embodiment of the present invention.
Figure 10B:
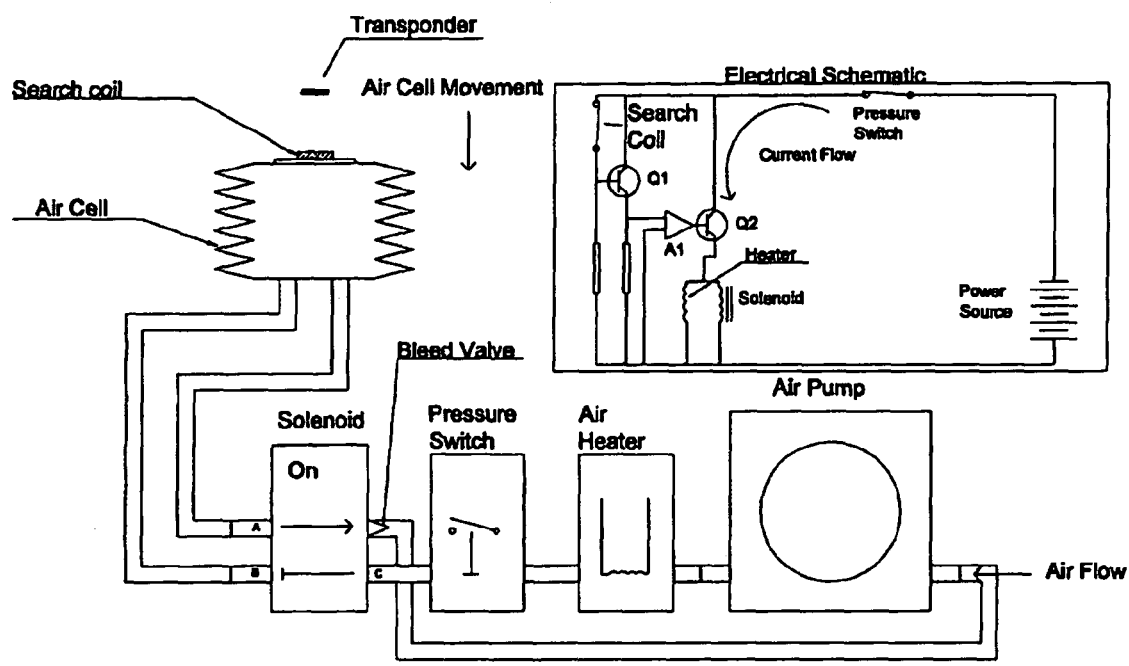
FIG. 10B is a schematic illustration of the mechanism of cell operation depicted in FIG. 10A, wherein the cell is transforming from the fill condition into the emptying condition.

Another preferred embodiment of the operation of a cell, in the form of an air cell, according to the present invention is illustrated in FIGS. 10A and 10B. In this embodiment, the air cell is subject to positive pressure to inflate. This increases the response time and enables the cell to lift a relatively larger weight. A programmed passive transponder is used to activate the air cell, solenoid vibration and air heater. According to this embodiment, the distance between the presence identification means or transponder and the sensing means or search coil can be greater than in the embodiment described in relation to FIGS. 9A and 9B. The transponder can activate the air cell through a thick layer of padding and bed clothes.

Solenoid vibration is provided by a switching solenoid that is pulse driven to provide vibration within the air cell. A heating means, such as an air heater or heating element, provides heat to the air in the cell and/or the cell.

The pressure switch depicted in FIGS. 10A and 10B is adapted to reduce the air flow by slowing the pump. FIG. 10B illustrates the air cell depicted in FIG. 10A in the air emptying condition having transformed from the air fill condition. Suction can additionally be provided to facilitate transformation to the air emptying condition.

An over-inflation inhibition means can also be incorporated into a cell according to this invention which is adapted to inhibit over-inflation of the cell. An example of an over-inflation inhibition means is a bleed valve.

In preferred embodiments, the system or interactive patient apparatus is adapted so that despite the fact that the distance between the presence identification means and the sensing means may increase, or the presence identification means and sensing means may be brought out of a predetermined distance from one another, due to, for example, deflation of an air cell, the system and/or apparatus nevertheless continues to operate such that the property sought to be altered in that particular instance (eg reduction in pressure) continues to be altered as such. This continues for a predetermined period or until such time as a further event occurs requiring a different and/or additional property to be altered for the same cell and/or a property or properties to be altered for a different cell or cells.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An interactive patient system comprising:
   a patient support apparatus;
   sensing means associated with the patient support apparatus, the sensing means in the form of a programmable transponder configured to send and receive a radio-frequency location signal;
   presence identification means associated with a region of a patient, the presence identification means including a programmable transponder and memory, the programmable transponder and memory releasably attachable to skin or clothing of a patient and adapted to receive a radio-frequency location signal and send location data and other treatment data stored in the memory via a radio-frequency signal; and
   altering means configured to alter a property of the patient support apparatus in proximity to the presence identification means upon identification of an activity signal, thereby effecting an activity in the vicinity of the region of the patient;

wherein the activity signal is associated with transmission or identification of at least one radio-frequency location signal and other data stored in the memory between the sensing means and the presence identification means.

2. The system according to claim 1 wherein transmission of at least one radio-frequency location signal as between the sensing means and the presence identification means is effected when the presence identification means and the sensing means are brought within a predetermined distance from one another.

3. The system according to claim 1 wherein the patient support apparatus is selected from the group consisting of a bed, a mattress, an underlay, an orthosis, splint, calliper, and crutch.

4. The system according to claim 3 wherein the patient support apparatus is a mattress.

5. The system according to claim 1 wherein the property is selected from the group consisting of pressure, temperature, movement and vibration.

6. The system according to claim 5 wherein the property is pressure and the activity is a reduction in pressure.

7. The system according to claim 5 wherein the property is vibration.

8. The system according to claim 1 wherein the sensing means includes its own power supply.

9. The system according to claim 8 wherein the power supply is a battery.

10. The system according to claim 1 wherein the sensing means is located proximal a region of the patient when the apparatus is in use.

11. The system according to claim 1 wherein the presence identification means is configured to send a radio-frequency location signal when the presence identification means is within a predetermined distance from the sensing means.

12. The system according to claim 1 further including control mean's configured to identify an instruction from the presence identification means or the sensing means and to send the activity signal to the altering means to alter the property of the apparatus.

13. The system according to claim 1 wherein the patient support apparatus includes a plurality of cells, and each cell includes at least one sensing means.

14. The system according to claim 13 wherein each cell further includes at least one altering means.

15. The system according to claim 14 wherein movement of the region of the patient relative to the apparatus results in different cells having a property altered at different times.

16. The system according to claim 1 wherein the altering means is configured to alter one or more properties of the patient support apparatus.

17. A method for providing a directed response to a region of a patient, the method comprising:

providing an interactive patient system including a programmable transponder and a patient support apparatus, the interactive patient system being according to claim 1;

programming the transponder to transmit treatment data and routines by radio frequency when in proximity to the patient support apparatus;

attaching the presence identification means adjacent the region of the patient;

placing the patient on, or in operative proximity to, the patient support apparatus; and enabling the altering means to alter a property of the apparatus in proximity to the region of the patient in response to the activity signal, thereby providing a directed response to the region of the patient.

* * * * *